United States Patent [19]

Scott et al.

[11] Patent Number: 5,227,350
[45] Date of Patent: Jul. 13, 1993

[54] FLUORINATION CATALYST REGENERATION

[75] Inventors: John D. Scott; Pravin K. Dattani, both of Cheshire, England

[73] Assignee: Imperial Chemical Industries PLC, London, England

[21] Appl. No.: 913,998

[22] Filed: Jul. 17, 1992

Related U.S. Application Data

[63] Continuation of Ser. No. 759,596, Sep. 16, 1991, abandoned.

[30] Foreign Application Priority Data

Sep. 14, 1990 [GB] United Kingdom ............... 9020084

[51] Int. Cl.$^5$ .................. B01J 27/32; B01J 38/46; B01J 38/44; C07C 17/00
[52] U.S. Cl. ........................... 502/36; 502/37; 570/168; 570/169
[58] Field of Search ................. 502/36, 37, 228

[56] References Cited

U.S. PATENT DOCUMENTS

| | | | |
|---|---|---|---|
| 2,745,886 | 5/1956 | Ruh et al. | 502/228 |
| 3,660,307 | 5/1972 | Scherer et al. | 502/36 |
| 4,145,311 | 3/1979 | von Halasz et al. | 502/36 |
| 4,578,369 | 3/1986 | Muller et al. | 502/36 |

FOREIGN PATENT DOCUMENTS

0166336 1/1986 European Pat. Off. .
2006080 12/1969 France .

*Primary Examiner*—Paul E. Konopka
*Attorney, Agent, or Firm*—Cushman Darby & Cushman

[57] ABSTRACT

A method for regenerating a used fluorination catalyst such as a chromium-containing compound comprises contacting the used catalyst at a temperature of 300° C. to 500° C. with a mixture of an oxidizing agent, especially air, and hydrogen fluoride and optionally an inert diluent such as nitrogen, said mixture containing up to 30% of oxidizing agent on a molar basis. The method obviates chromium loss during regeneration/refluorination of spent catalyst and provides heated hydrogen fluoride for use directly in fluorination reactions.

9 Claims, No Drawings

FLUORINATION CATALYST REGENERATION

This is a continuation of application Ser. No. 07/759,596, filed on Sep. 16, 1991, which was abandoned upon the filing hereof.

This invention relates to a chemical process and more particularly to a process for the regeneration of a fluorination catalyst.

It is well known to react hydrogen fluoride with various organic compounds for the purpose of introducing one or more fluorine atoms. For example, it is known to react hydrogen fluoride with various $C_2$ compounds such as trichloroethylene or 1,1,1-trifluoro-2-chloroethane in order to make 1,1,1,2-tetrafluoroethane (HFA 134a).

It is customary to employ a fluorination catalyst in these reactions, several types of catalyst having been described in the prior art. Unfortunately, the activity of these catalysts deteriorates during the course of the fluorination and it becomes necessary to subject the exhausted or spent catalyst to a regeneration treatment. This usually involves contacting the used catalyst with air in order to burn off organic contaminants. Such a procedure is highly exothermic and in order to avoid expensive cooling systems and allow the use of an adiabatic catalyst bed the supply of air is often controlled by use of a diluent; nitrogen is commonly used as the diluent. After use in this way the nitrogen is vented to atmosphere but the presence of organic impurities can cause environmental problems.

It has now been found that spent fluorination catalysts may be advantageously regenerated by the use of mixtures of air or other oxidising agent and hydrogen fluoride, the regeneration off-gases containing hydrogen fluoride being utilisable in fluorination reactions.

For simplicity the invention will be described with reference to air as oxidising agent but it is to be understood that any oxidising agent comprising oxygen may be used instead of air.

According to the invention there is provided a method for the regeneration of a fluorination catalyst after use in a fluorination reaction, said method comprising contacting said used catalyst at a temperature in the range from 300° to 500° C. with a mixture of air and hydrogen fluoride and optionally an inert diluent containing up to 30% of air on a molar basis.

Fluorination catalysts which may be regenerated using the method of the invention particularly include catalysts that have been used to catalyse the reaction of hydrogen fluoride with halogenated hydrocarbons, especially chlorinated olefins such as trichloroethylene or chlorinated alkanes such as 1,1,1-trifluoro-2-chloroethane. Suitable fluorination catalysts have been fully described in the prior art and include various inorganic compounds, for example oxides and halides of metals such as aluminium, cobalt, manganese, iron and especially chromium. Suitable chromium-containing catalysts include the oxide, hydroxide, halides, oxyhalides, inorganic acid salts, basic chromium fluoride and the catalysts described in our United Kingdom Patent No 1,307,224.

The composition of the mixtures used to regenerate the catalysts may vary over a wide range depending to a large extent upon whether a diluent such as nitrogen is included in the mixture. Where a diluent such as nitrogen is not present in the mixture, the hydrogen fluoride comprises at least 70% of the mixture on a molar basis, the hydrogen fluoride content suitably being from 70% to 99.9% on a molar basis. Where a diluent is present in the mixture, the hydrogen fluoride and the diluent together comprise at least 70% of the mixture on a molar basis and the content of hydrogen fluoride is preferably such that the molar ratio of hydrogen fluoride: air is at least 0.1:1. Thus the mixture contains hydrogen fluoride and air in a mole ratio of at least 0.1:1, preferably at least 1:1 and more preferably at least 2:1 for example from 2–100:1. In general the mole ratio of hydrogen fluoride:air decreases as the content of diluent increases.

Preferred compositions also depend to some extent upon the type of catalyst bed used. For adiabetic beds, air/HF mixtures containing up to 10% air on a molar basis are preferred, typical mixtures containing about 2% air. For tube cooled reactors, higher air contents, up to 30% on a molar basis, can be tolerated.

The air/hydrogen fluoride/optional diluent mixture may also contain small amounts of organic materials, for example up to 1% on a molar basis of the starting materials and/or intermediates and/or products of the fluorination process. Thus, for example, the hydrogen fluoride and/or the diluent may be recycled from the products of the fluorination reaction.

Treatment of the spent catalyst with the air/HF/diluent mixture may be continued for the time required to provide the desired degree of catalyst regeneration, preferred temperatures being in the range from 330° to 450° C. The regeneration off gases are then preferably recycled, without cooling, to the fluorination reactor or are used in another fluorination reaction.

In prior art processes, it is usual to give the regenerated catalyst a prefluorination treatment prior to its reintroduction into the fluorination reaction. An advantage of the catalyst regeneration method of the invention is that since hydrogen fluoride is used in the regeneration process, no additional prefluorination treatment is necessary. A further advantage of the method of the invention, due at least in part to the avoidance of the need for a prefluorination treatment of the regenerated catalyst, is that no significant loss of chromium occurs during the regeneration of the catalyst and its reintroduction into service; oxidation of Cr(III) compounds to volatile and toxic Cr(VI) compounds, a feature of many prior catalyst regeneration methods, is obviated or at least minimised.

In a preferred embodiment of the invention, a mixture of hydrogen fluoride and a fluorinatable material is fed alternately to two catalyst beds located in parallel, the bed not in use being subjected to the regeneration method of the invention.

The invention is illustrated but not limited by the following Examples.

EXAMPLE 1

A chromia fluorination catalyst, after use in a process for the production of 1,1,1,2-tetrafluoroethane by the fluorination of 1,1,1-trifluoro-2-chloroethane, is heated over 2 hours to 400° C. in an atmosphere of hydrogen fluoride. A 50:1 molar mixture of hydrogen fluoride and air is passed over the catalyst for 6 hours at 400° C. An exotherm of about 50° C. in the catalyst bed is observed.

When regeneration is complete, the air flow is stopped and the catalyst is cooled over 2 hours to an appropriate fluorination temperature.

EXAMPLE 2

A 200 g sample of a chromia-based catalyst was charged into a 2" diameter Inconel reactor housed in an oven. The catalyst was heated to 350° C. and exposed to a 1,1-dichloro-2,2,2-trifluoroethane (133a) and HF feed in a molar ratio of 1:3.5 for 16 hours. The gases from the reactor were passed into an aqueous batch scrubber and the chromium level in the scrubber was analysed for total chromium content using atomic adsorption analysis. No chromium was detected in the scrubber solution after 16 hours; see Sample 1 in Table 1.

The 133a and HF feeds were stopped after 16 hours and the reactor was purged with nitrogen and heated to 400° C. The scrubber water was changed and the reactor was then fed with a 20:1 molar ratio mixture of HF and Air. The product from the reactor was passed into an the aqueous scrubber and the chromium level in the scrubber analysed as before. The total level of chromium accumulated in the scrubber in the first 16 hours of regeneration was measured and found to be non-detectable; see Sample 2 in Table 1. In a further study the catalyst was regenerated as above for 72 hours instead of 16 hours, again with no chromium detected in the scrubber; see Sample 3.

The method of the invention was then compared with a conventional regeneration and refluorination sequence. This regeneration sequence firstly involved heating the catalyst in air, followed by a separate refluorination treatment with HF. Exposing an air regenerated catalyst to HF was found to result in high levels of chromium loss; see Samples 5 and 6 and the comparable study 7 and 8, Samples 6 and 8 using different HF flow rates as shown by contact times with the catalyst.

Following a period of reaction, see Sample 9, two examples of nitrogen diluted air regenerations were performed and these are exemplified by Samples 10 and 11 and 12 and 13. Substantial levels of chromium were lost from the catalyst charge.

Following the final reaction period, see Sample 14, a series of HF:Air regenerations were performed under higher flow rate and shorter catalyst contact time conditions. Again very low levels of chromium loss were observed even at the highest flow rates; see Sample 15 to 18.

Finally a lower HF:Air ratio of 1:1 demonstrated that chromium loss became significant at the reduced HF:Air ratio; see Sample 19.

TABLE 1

| Sample | FEED | Contact Time (secs) | TEMP °C. | Time (hours) | Chromium Loss (g) |
|---|---|---|---|---|---|
| 1 | 133a:HF 1:3.5 | 159 | 350 | 16 | 0.000 |
| 2 | HF:Air 20:1 | 181 | 400 | 16 | 0.000 |
| 3 | HF:Air 20:1 | 181 | 400 | 72 | 0.000 |
| 4 | 133a:HF 1:3.5 | 159 | 350 | 16 | 0.000 |
| *5 | Air | 410 | 350 | 18 | 0.000 |
| *6 | HF | 205 | 350 | 16 | 0.187 |
| *7 | Air | 410 | 350 | 18 | 0.002 |
| *8 | HF | 20 | 350 | 4 | 0.321 |
| 9 | 133a:HF 1:3.5 | 173 | 300 | 8 | 0.000 |
| *10 | N2:Air 10:1 | 37 | 350 | 16 | 0.005 |
| *11 | HF | 20 | 350 | 2 | 0.465 |
| *12 | N2:Air 10:1 | 35 | 400 | 16 | 0.006 |
| *13 | HF | 20 | 350 | 2 | 0.220 |
| 14 | 133a:HF 1:3.5 | 173 | 300 | 16 | 0.000 |
| 15 | HF:Air 20:1 | 181 | 400 | 16 | 0.000 |
| 16 | HF:Air 20:1 | 90 | 400 | 23 | 0.001 |
| 17 | HF:Air 20:1 | 45 | 400 | 23 | 0.000 |
| 18 | HF:Air 20:1 | 30 | 400 | 23 | 0.000 |
| 19 | HF:Air 1:1 | 90 | 400 | 23 | 0.010 |

*For Comparison

EXAMPLE 3

10 kg of chromia fluorination catalyst were charged to a 2" diameter salt cooled reactor. The catalyst was conditioned by passage of 5 kg of HF at 300° C. and then 133a was added to the HF feed to give a molar feed ratio of 3.0:1 HF:133a. With the reactor pressure at 13 bar g, the catalyst temperature was increased to 320° C. to achieve a target 12% conversion of 133a to 134a. The contact time in the reactor under reaction conditions was approximately 10 seconds. As the catalyst deactivated, the reactor temperature was raised to maintain the 12% 134a reaction yield. After 90 hours of operation the catalyst had deactivated and the 133a feed was switched off. The reactor was heated to 380° C., with the catalyst purging in the HF feed.

Air was then added to the HF feed to make a mixed HF:Air molar feed ratio of 40:1. The catalyst was regenerated for 16 hours under these conditions before the air feed was stopped and the reactor returned to 300° C. The 133a feed was restarted to give the original 3:1 HF:133a molar feed ratio. The catalyst temperature was again increased when necessary to maintain a 12% 134a yield. The operating period following the HF:Air regeneration was 92 hours. This reaction and HF/Air regeneration procedure was repeated for a further 3 cycles.

The efficiency of the HF:Air regeneration method, as measured by the length of the subsequent reaction period, was then compared with Nitrogen:Air regenerations. Following the 5th operational period, the regeneration was again performed at 380° C., but the HF flow was replaced with an equal molar flow of nitrogen to generate a 40:1 N2:Air mixture. After 16 hours of regeneration the catalyst was returned to 300° C., refluorinated with HF and fed with 133a as described above. As seen from the results in Table 2, the operating period of the catalyst was observed to decrease progressively on using the N2:Air regeneration method.

TABLE 2

| | | Operating Period hours |
|---|---|---|
| Fresh Catalyst | | 90 |
| After HF:Air | Regeneration 1 | 92 |
| After HF:Air | Regeneration 2 | 100 |
| After HF:Air | Regeneration 3 | 100 |
| After HF:Air | Regeneration 4 | 100 |
| COMPARISON | | |
| After N2:Air | Regeneration 5 | 93 |
| After N2:Air | Regeneration 6 | 54 |
| After N2:Air | Regeneration 7 | 66 |
| After N2:Air | Regeneration 8 | 47 |
| After N2:Air | Regeneration 9 | 36 |
| After N2:Air | Regeneration 10 | 22 |
| After N2:Air | Regeneration 11 | 21 |

EXAMPLE 4

10 kg of catalyst were charged to an adiabatic reactor. A preheated nitrogen supply was used to raise the catalyst temperature in the adiabatic reactor to 250° C. The catalyst was then fluorinated using 5 kg of HF as described in example 3. Nitrogen was added to the HF prefluorination feed, to limit the catalyst temperature rise to less than 100° C. The nitrogen diluent was removed and the catalyst temperature was adjusted to 300° C. using the HF feed. 133a was then added to the HF feed to generate a reaction mixture with an HF:133a molar feed ratio of 3:1. The catalyst temperature was raised by adjusting the feed inlet temperature until the target 12% 134a yield was achieved. Target conversion was achieved at an inlet temperature of approximately 330° C. The reaction selectivity of 98-99% 134a was maintained for 100 hours as the catalyst temperature was raised to compensate for catalyst deactivation.

The catalyst was then reactivated according to the invention. This involved stopping the 133a feed and using the 350° C. preheated HF feed to adjust the catalyst temperature for regeneration. Air was gradually introduced into the HF feed. The adiabatic temperature rise during regeneration increased the catalyst temperature from 350° C. to 380°-400° C., when using a HF:Air molar feed ratio of 20-50:1. By taking samples from the downstream aqueous scrubber system, the chromium release during the catalyst regeneration was determined.

After approximately 5 hours of regeneration, the catalyst in the reactor cooled to 350° C. as the regeneration reaction subsided. The air feed was then stopped and the HF feed temperature set at 330° C., ready for the start of the next 133a reaction cycle. The 133a feed was restarted and the reactivated catalyst was found to give a 134a yield of 12-14% at 330° C.

The chromium based catalyst was successfully reactivated with non-detectable levels of chromium released to the down-stream scrubber system. The regeneration also avoided introducing large quantities of nitrogen to the down-stream equipment; this latter feature being extremely valuable when two or more reactors are used in parallel with a common vent system, as the unreacted feeds with 134a and HCl products from the operating reactors are not diluted with large quantities of nitrogen employed to regenerate the off-line reactor.

EXAMPLE 5

Comparative Example

The regenerated catalyst from Example 4 was operated for 92 hours. The 133a feed was then stopped and the HF preheater set at 350° C. The HF flow was then replaced by the same flow of nitrogen. When the catalyst temperature had reached 350° C., air was added to the nitrogen to regenerate the catalyst. A 50° exotherm was generated using a $N_2$:Air molar feed ratio of 20-50:1 and this exotherm subsided in 5-6 hours, after which the air flow was stopped and the HF flow was restarted. The chromium levels in the scrubber system were monitored and the results indicated that 15 g of chromium had been lost from the reactor during catalyst regeneration and refluorination.

We claim:

1. A method for the regeneration of a fluorination catalyst after use in a fluorination reaction consisting essentially of contacting the used catalyst at a temperature in the range from 300° C. to 500° C. with a mixture of an oxidizing agent and hydrogen fluoride containing up to 30% of the oxidizing agent on a molar basis.

2. A method as claimed in claim 1 wherein the oxidizing agent is air.

3. A method as claimed in claim 1 or claim 2 wherein the molar ratio of hydrogen fluoride:air in the mixture is at least 0.1:1.

4. A method as claimed in claim 3 wherein the molar ratio of hydrogen fluoride:air is from 2-100:1.

5. A method as claimed in claim 4 wherein the mixture contains from 70% to 99.9% of hydrogen fluoride on a molar basis.

6. A method as claimed in claim 4 wherein the mixture also contains an inert diluent.

7. A method as claimed in claim 4 wherein the temperature is in the range from 330° C. to 450° C.

8. A method as claimed claim 4 wherein the catalyst is a chromium-containing catalyst.

9. A method as claimed in claim 1 wherein said mixture comprises, on a molar basis, from 0.1% up to 30% of oxidizing agent and from 99.9% to 70% of hydrogen fluoride.

* * * * *